(12) United States Patent
Papaioannou

(10) Patent No.: US 9,289,180 B2
(45) Date of Patent: Mar. 22, 2016

(54) DYNAMIC BIPLANE ROENTGEN STEREOPHOTOGRAMMETRIC ANALYSIS

(71) Applicant: George Papaioannou, Great Neck, NY (US)

(72) Inventor: George Papaioannou, Great Neck, NY (US)

(*) Notice: Subject to any disclaimer, the term of this patent is extended or adjusted under 35 U.S.C. 154(b) by 0 days.

(21) Appl. No.: 14/324,823

(22) Filed: Jul. 7, 2014

(65) Prior Publication Data

US 2015/0150522 A1 Jun. 4, 2015

Related U.S. Application Data

(63) Continuation of application No. 13/936,829, filed on Jul. 8, 2013, now Pat. No. 8,770,838, which is a continuation of application No. 12/587,853, filed on Oct. 13, 2009, now Pat. No. 8,525,833.

(60) Provisional application No. 61/208,183, filed on Feb. 20, 2009, provisional application No. 61/104,970, filed on Oct. 13, 2008.

(51) Int. Cl.
| | |
|---|---|
| *H05G 1/02* | (2006.01) |
| *A61B 6/04* | (2006.01) |
| *A61B 6/00* | (2006.01) |
| *A61B 6/02* | (2006.01) |
| *A61B 5/11* | (2006.01) |

(52) U.S. Cl.
CPC .............. *A61B 6/0457* (2013.01); *A61B 6/022* (2013.01); *A61B 6/04* (2013.01); *A61B 6/4014* (2013.01); *A61B 6/4452* (2013.01); *A61B 6/4458* (2013.01); *A61B 6/4464* (2013.01); *A61B 6/466* (2013.01); *A61B 6/505* (2013.01); *A61B 5/1114* (2013.01); *A61B 6/4225* (2013.01); *A61B 6/4423* (2013.01); *A61B 6/486* (2013.01)

(58) Field of Classification Search
CPC ...... A61B 6/04; A61B 6/4014; A61B 6/4458; A61B 6/466; A61B 6/0457; A61B 6/505; A61B 6/022; A61B 6/4452; A61B 6/4464; A61B 5/1114; A61B 6/4225; A61B 6/4423; A61B 6/486
USPC ...................................... 378/20, 62, 193–198
See application file for complete search history.

(56) References Cited

U.S. PATENT DOCUMENTS

| | | | |
|---|---|---|---|
| 8,770,838 B2 * | 7/2014 | Papaioannou | 378/195 |
| 2002/0097831 A1 * | 7/2002 | Cheng | 378/20 |
| 2006/0029181 A1 * | 2/2006 | Chen et al. | 378/17 |

* cited by examiner

*Primary Examiner* — Courtney Thomas
(74) *Attorney, Agent, or Firm* — Michael Best & Friedrich LLP

(57) ABSTRACT

A medical imaging system includes a first x-ray image detector, a first x-ray generator, and a motorized turntable. The first x-ray image detector and the first x-ray generator are each mounted on a base and positioned opposite each other such that x-rays are projected from the first x-ray generator to the first x-ray image detector through a first imaging volume. The motorized turntable is positioned below the first imaging volume and between the first x-ray image detector and the first x-ray generator and is configured to rotate an imaging subject within the imaging volume.

19 Claims, 14 Drawing Sheets

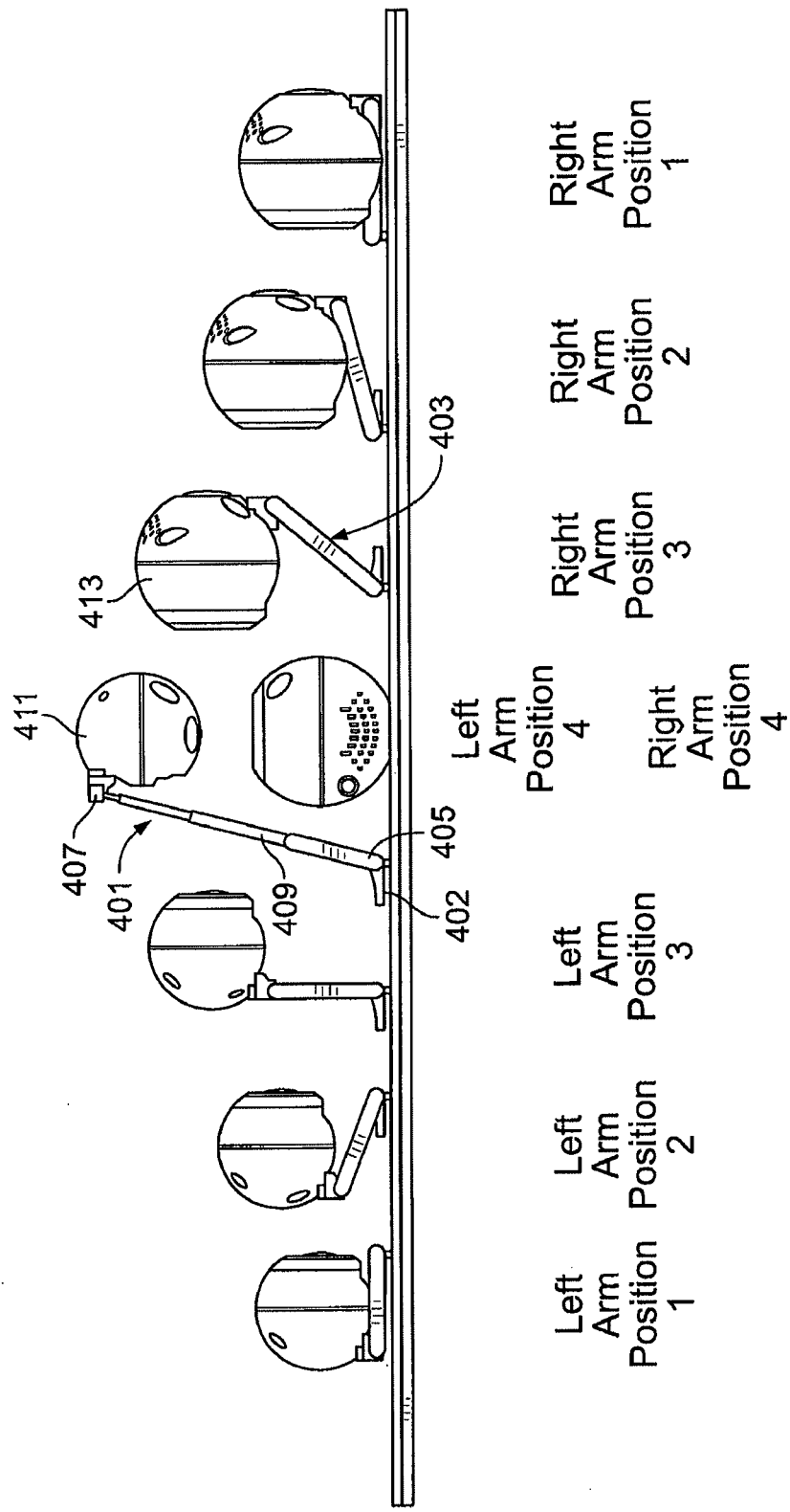

DYNAMIC BIPLANE ROENTGEN STEREOPHOTOGRAMMETRIC ANALYSIS

RELATED APPLICATIONS

The present application is a continuation of U.S. application Ser. No. 13/936,829, filed Jul. 8, 2013, which is a continuation of U.S. application Ser. No. 12/587,853, filed on Oct. 13, 2009, which claims priority to U.S. Provisional Application No. 61/104,970 filed on Oct. 13, 2008 and U.S. Provisional Application No. 61/208,183 filed on Feb. 20, 2009, the entire contents of all of which are incorporated herein by reference.

BACKGROUND

Embodiments of the invention relate to computer-aided, radiography image capture and processing technologies.

Medical radiography generally refers to the use of x-rays (i.e., Roentgen radiation) to view objects inside the human body such as, for example, bones. In current radiographic technologies, x-rays are projected from a source, through a body and are detected on a photographic film or semiconductor diode arrays. The static images are then viewed on the film or are captured as digital images to be viewed on a monitor.

SUMMARY

Embodiments of the invention provide methods and systems for the computer-aided capture and processing of medical images without the use of a c-arm. A dynamic three-dimensional model of an imaging subject is created using stereophotogrammetric reconstruction techniques. Some embodiments of the invention provide dynamic imaging (e.g., videoradiography) that enables a healthcare professional to view the skeletal system in motion. Some embodiments offer the capability to perform volume acquisition and modeling using both tomosynthesis and cone-beam computed tomography (c-CT).

In one embodiment, the invention provides a method of generating a three-dimensional volumetric representation of a subject. The method includes capturing a first image of the subject with a first capture device from a first perspective, accessing a stored volumetric model of the subject, and approximating a first orientation of the stored volumetric model that corresponds to the first perspective. A digitally simulated radiograph is generated from the stored volumetric model and compared to the captured first image. A second image is also captured at the same time as the first picture, but from a different perspective. A second orientation of the stored volumetric model is approximated that corresponds to the second image. A second digitally simulated radiograph is generated and compared to the second image. Based on the approximated orientations, a three-dimensional volumetric representation of the subject is generated by positioning the stored volumetric model according to the first orientation and the second orientation.

In some embodiments, the method includes calculating a correlation score for the approximated first orientation and calculating a correlation score for a subsequent approximated first orientation. A best match orientation is selected based on the correlation score.

In some embodiments, a plurality of images is captured of a moving subject over time. The method then includes generating a three-dimensional volumetric representation of the moving subject by positioning the stored volumetric model according to the first orientation and the second orientation over a period of time.

Other aspects of the invention will become apparent by consideration of the detailed description and accompanying drawings.

BRIEF DESCRIPTION OF THE DRAWINGS

FIG. 4 is illustrates various orientations of the x-ray emitter or the image detector mounted to a robotic arm according to one embodiment of the invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
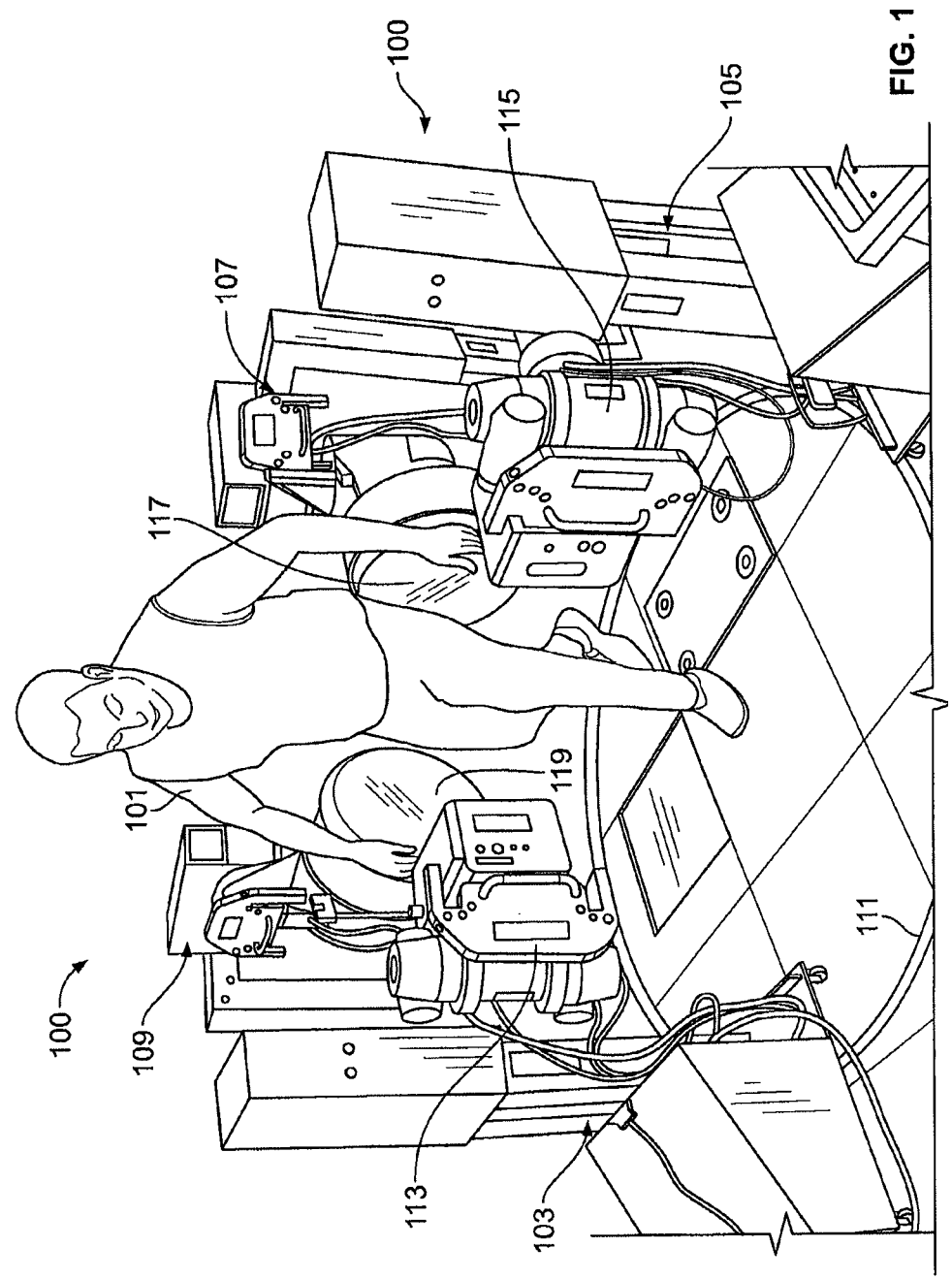
FIG. 1 is a perspective view of a human subject moving within the imaging volume of an imaging system according to one embodiment.

FIG. 1 shows a human subject 101 moving within the imaging volume of an imaging system 100 according to a first embodiment. As described in detail below, the system 100 provides for dynamic imaging. Therefore, a user of the system 100 is able to capture, save, and analyze images of the subject in motion. The system shown in FIG. 1 includes four robotic arms 103, 105, 107, 109 mounted to a circular track on the floor 111. In FIG. 1, the arms are positioned at 90° intervals relative to each other around the circular track. Each robotic arm is equipped with a separate motor such that the angle of orientation can be changed in certain imaging applications. In some embodiments the angle between the imaging planes can vary from 30 degrees to 180 degrees. In other embodiments, the track 111 is equipped with a motor system to move the four arms around the imaging volume without changing the angle of the arms relative to each other.

Mounted on top of the first and second robotic arms 103, 105 is a first and second x-ray generator 113, 115, respectively. On the third and fourth arms 107, 109 is a first and second x-ray detector 117, 119. In the embodiment shown, the x-ray generators 113, 115 are 150 kVp generators with a 0.09 mm focal spot size, and each x-ray detector 117, 119 includes a 16 or 19-inch image intensifier with vertically aligned 10:1 grids for scatter reduction and a high-speed digital camera. However, in alternative embodiments, other generators and detectors can be used and one or both of the x-ray detectors may include a scintillator and a digital camera. The use of a scintillator allows images of very high resolution to be captured whereas the use of image intensifiers allows images to be captured at a high rate, high resolution and with a relatively low x-ray dosage.

Each x-ray detector 117, 119 is positioned at the opposite side of the circular track 111 from an x-ray generator 113, 115. The imaging volume is defined such that the distance between the x-ray generator and the image intensifier and can vary between approximately 1.2 meters and 1.8 meters. This configuration allows for data acquisition with image resolution as high as 2500×1800 pixels at acquisition rates as high as 1000 frames/s. Radiation exposure at this high acquisition rate can be as low as 40 kVP at 50 mA for 0.01 s to 30 s without affecting the image quality. This configuration provides 0.1 mm in translational accuracy and 0.5 degrees in rotational accuracy in assessing skeletal and joint kinematics at high speeds of motion (such as those involved in jumping, impact, running, throwing tasks).

Each device (e.g., the x-ray generator or x-ray detector) 113, 115, 117, 119 is pivotably mounted to one of the four robotic arms 103, 105, 107, 109. Each arm is equipped with an electric motor (not pictured) to controllably change the angle of the device relative to the robotic arm. Each robotic arm also includes a plurality of telescoping segments 121 that can extend or lower the height of the device mounted to the arm. In some embodiments, a controller (not pictured) is programmed to change the pivot angle of the device in response to a change in the height of the robotic arm to ensure that each x-ray generator 113, 115 remains pointed toward its corresponding x-ray detector 117, 119. In other embodiments, the system operator manually adjusts the devices to their appropriate angles. The controller can be integrated into the system and specifically designed for the purpose of manipulating the robotic arms. Alternatively, the controller can be in the form of a personal computer.

Figure 2:
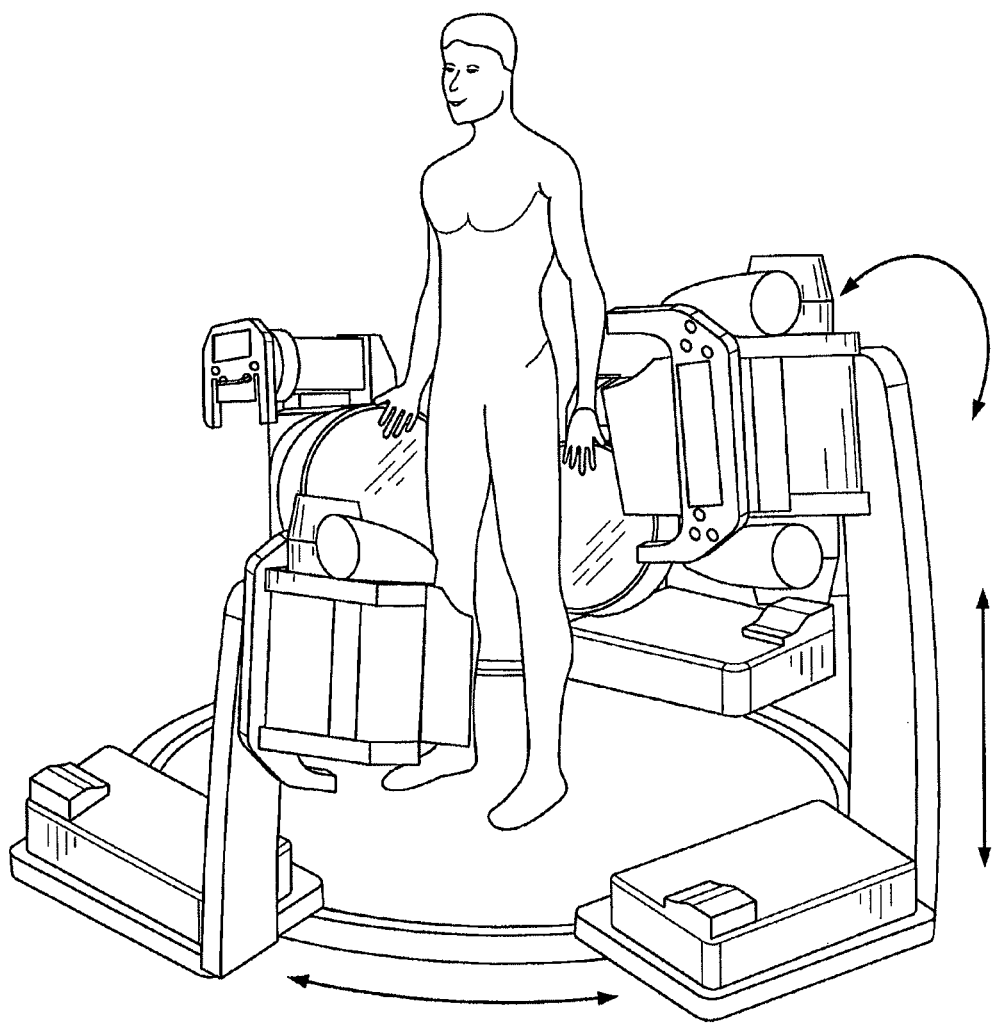
FIG. 2 is another perspective view showing the adjustable positions of a robotic arm according to the embodiment of FIG. 1.

FIG. 2 shows some of the changes in position that are possible using the system 100 of FIG. 1. As described above, the height of each robotic arm can be raised or lower and the pivot angle of the device relative to the robotic arm can be increased or decreased. Furthermore, the robotic arms can be moved around the subject along the track. In some embodiments, such as the one shown in FIG. 3, the system includes a turntable positioned within the imaging volume. In such embodiments, the orientation of the x-ray devices relative to the imaging subject is changed by rotating the imaging subject instead of rotating the robotic arms and the x-ray devices.

Figure 3:
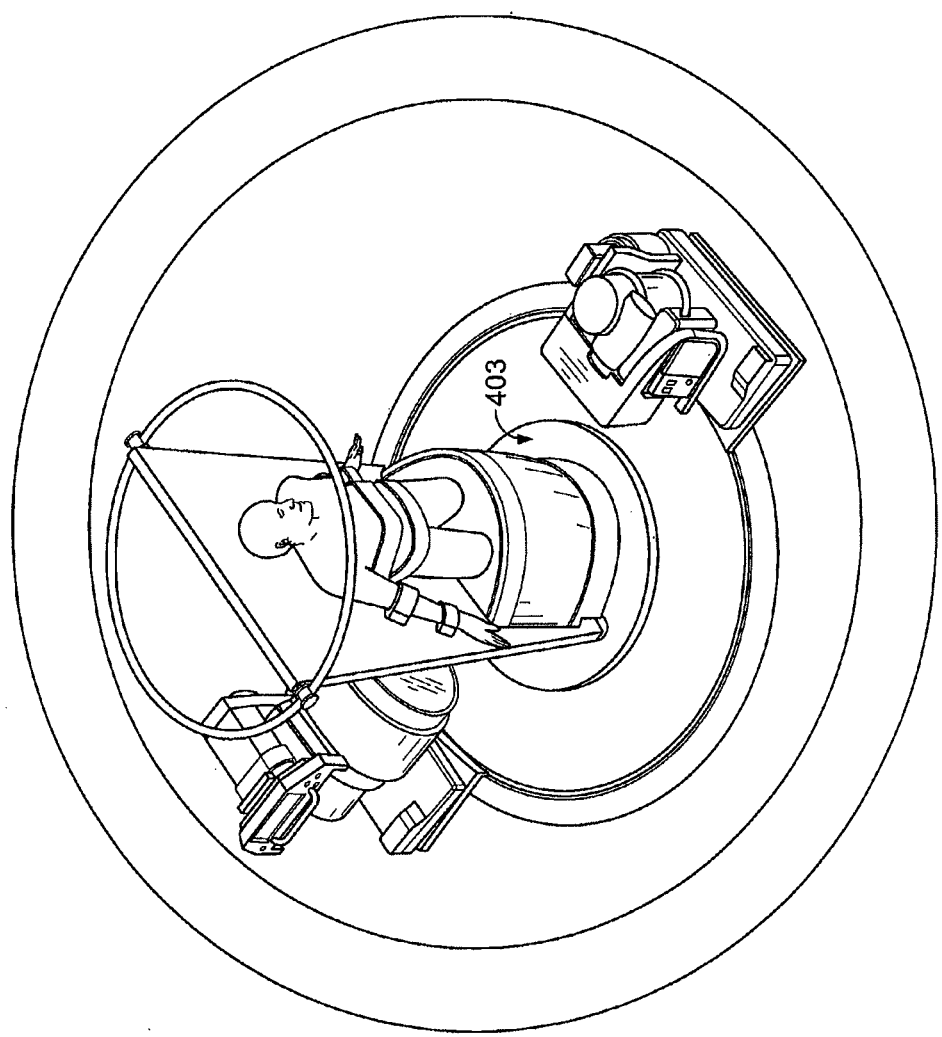
FIG. 3 is a perspective view of an imaging system that includes a turntable for rotating a subject within the imaging volume according to one embodiment of the invention.

Alternatively, the system shown in FIG. 3 can rotate the robotic arms around the imaging volume at the same time that the turntable rotates the imaging subject in the opposite direction. This form of tomosynthesis allows for more rapid data acquisition Although the robotic arms in FIG. 1 are only capable of raising, lowering, and pivoting the x-ray device mounted thereto, the robotic arms in other embodiments are capable of additional articulation. FIG. 4 shows a pair of robotic arms 401, 403 in four different positions. An x-ray generator 411 is mounted to the first arm 401 and an x-ray detector 413 is mounted to the second arm 403. The first robotic arm 401 includes a first pivot 405 between the robotic arm 401 and the base 402 and a second pivot 407 between the robotic arm 401 and the x-ray generator 411. Each pivot 405, 407 includes an electric motor (not pictured) for changing the position of the robotic arm 401 relative to the base 402 and for changing the position of the x-ray generator 411 relative to the robotic arm 401. The first robotic arm 401 also includes a plurality of telescoping segments 409 to change the height of the x-ray generator 411. Although reference numerals are not illustrated, the second robotic arm 403 includes similar pivots, motors, and telescoping segments.

The motorized pivots and telescoping segments allow the robotic arms to adjust the height, direction, or perspective angle of the imaging volume. In the first position (position 1), the robotic arms 401, 403 position the x-ray generator 411 and the x-ray detector 413 at the lowest height. The first pivot 405 positions the robotic arm 401 at a nearly zero-degree angle to the base 402. The second pivot 407 positions the x-ray generator 411 at a nearly zero-degree angle to the robotic arm 401. The second robotic arm 403 is similarly articulated such that the x-ray detector 413 is positioned opposite the x-ray generator 411. In the second and third positions (position 2 and position 3), the angles of the first and second pivots 405, 407 are increased to raise the height of the x-ray generator 411 while keeping the x-ray generator 411 horizontal.

Although the x-ray generator 411 and the x-ray detector 413 are kept horizontal in positions 1, 2, and 3. The motorized pivots and telescoping segments allow the angle of the x-ray generator 411 and the x-ray detector to be changed in order to alter the perspective angle of the resulting x-ray image. As illustrated in the fourth position (position 4) of FIG. 4, the angle of the second pivot 407 can be decreased while the angle of the first pivot 405 is decreased to alter the perspective angle of the x-ray generator 411. In the fourth position, the first robotic arm 401 positions the x-ray generator 411 vertically downward while the second robotic arm 403 positions the x-ray detector 413 vertically upward. The first and second robotic arms 401, 403 can be similarly positioned such that the x-ray generator 411 is directed vertically upward and the x-ray detector 413 is directed vertically downward. Furthermore, the motorized pivots and telescoping segments can manipulated provide a 180-degree range of motion between the two vertical positions (vertical upward and vertical downward).

The robotic arms illustrated in FIG. 4 can be manipulated to move the x-ray generator 411 and the x-ray detector 413 in almost any geometry imaginable. For example, the robotic arms can be moved in a horizontal or vertical sweeping pattern. Such a movement allows imaging of a body part while avoiding the spatial distortion that normally occurs in the corners of volume data acquired during tomosyntheis. Furthermore, by rotating both the robotic arms and the imaging subject independently and synchronously, as described above, an image can be captured that is of comparable quality to other CT systems while reducing the image capture time and, therefore, reducing the radiation exposure.

The range of motion illustrated in FIG. 4 allows the perspective angle and the height of the imaging volume to be altered depending upon the position of the intended imaging subject. For example, the x-ray generator 411 and x-ray detector 413 can be repositioned when the human subject is performing a task such as running, jumping, or throwing. The ability to manipulate the beam penetration angle allows for the monitoring and analysis of in-vivo joint kinematics under physiologically correct loading and motion.

Figure 5A:
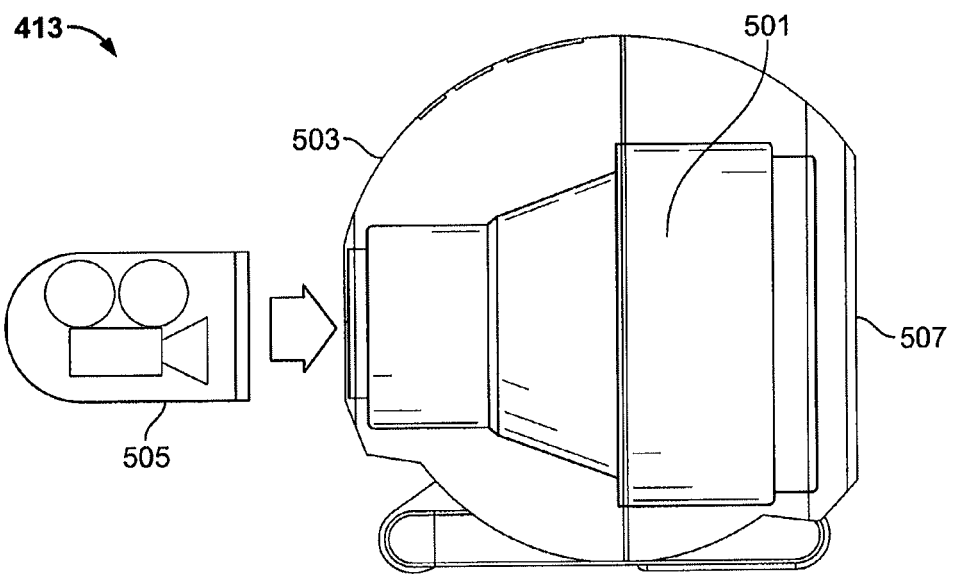
FIG. 5A is a side view of an x-ray detector according to the embodiment of FIG. 4.

As shown in FIG. 5A, an image intensifier 501 of an x-ray detector 413 is housed inside of a spherical housing 503. The spherical housing 503 is waterproof and provides a smooth surface to allow for easy cleaning of the housing 503 in a sterile hospital environment. A digital camera 505 is cased in a PVC jacket lined with rubber. The digital camera 505 is attached to the housing 503 by screw threading or another clamping mechanism. This allows for multiple cameras to be interchanged depending upon the specific application for which the system is being used. For example, a user may use one camera for static CT volumetric rendering and a different camera for dynamic radiographic imaging. The housing also includes a lens 507 through which x-rays enter the housing 503.

Figure 5B:
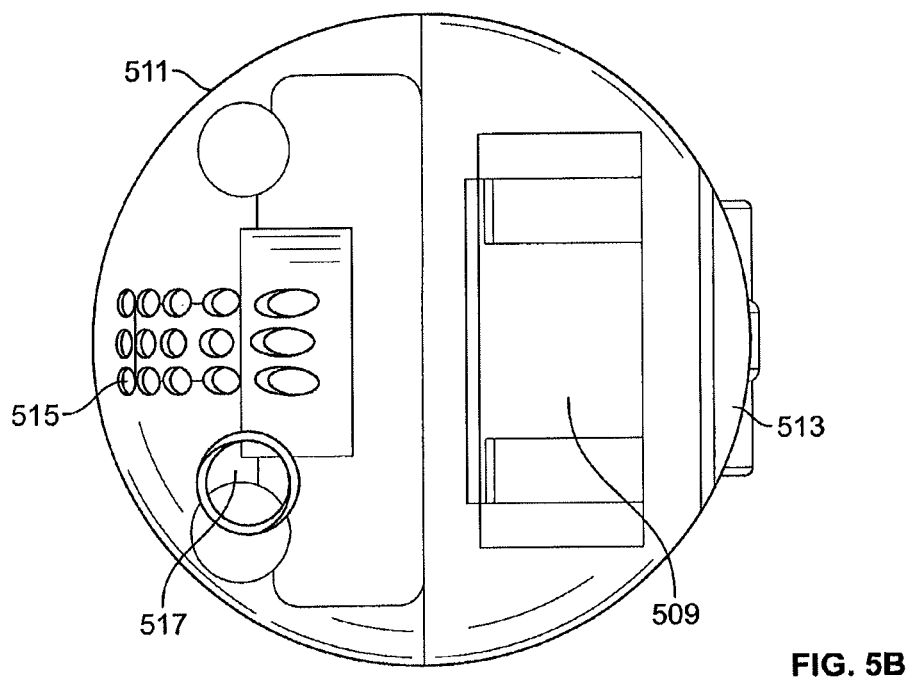
FIG. 5B is a transparent top view of an x-ray generator according to the embodiment of FIG. 4.

FIG. 5B is an overhead view of an x-ray generator 411. The x-ray generator 411 includes an x-ray source 509 enclosed within a housing 511. Like the x-ray detector 413, the housing 511 of the x-ray generator is spherical and includes a lens and collimator 513. X-rays generated by the x-ray source 509 are emitted through the lens and collimator 513 and projected through an imaging subject. The housing also includes a plurality of openings 515 to provide for ventilation and an opening 517 to provide access for power cords or other cabling.

Figure 6:
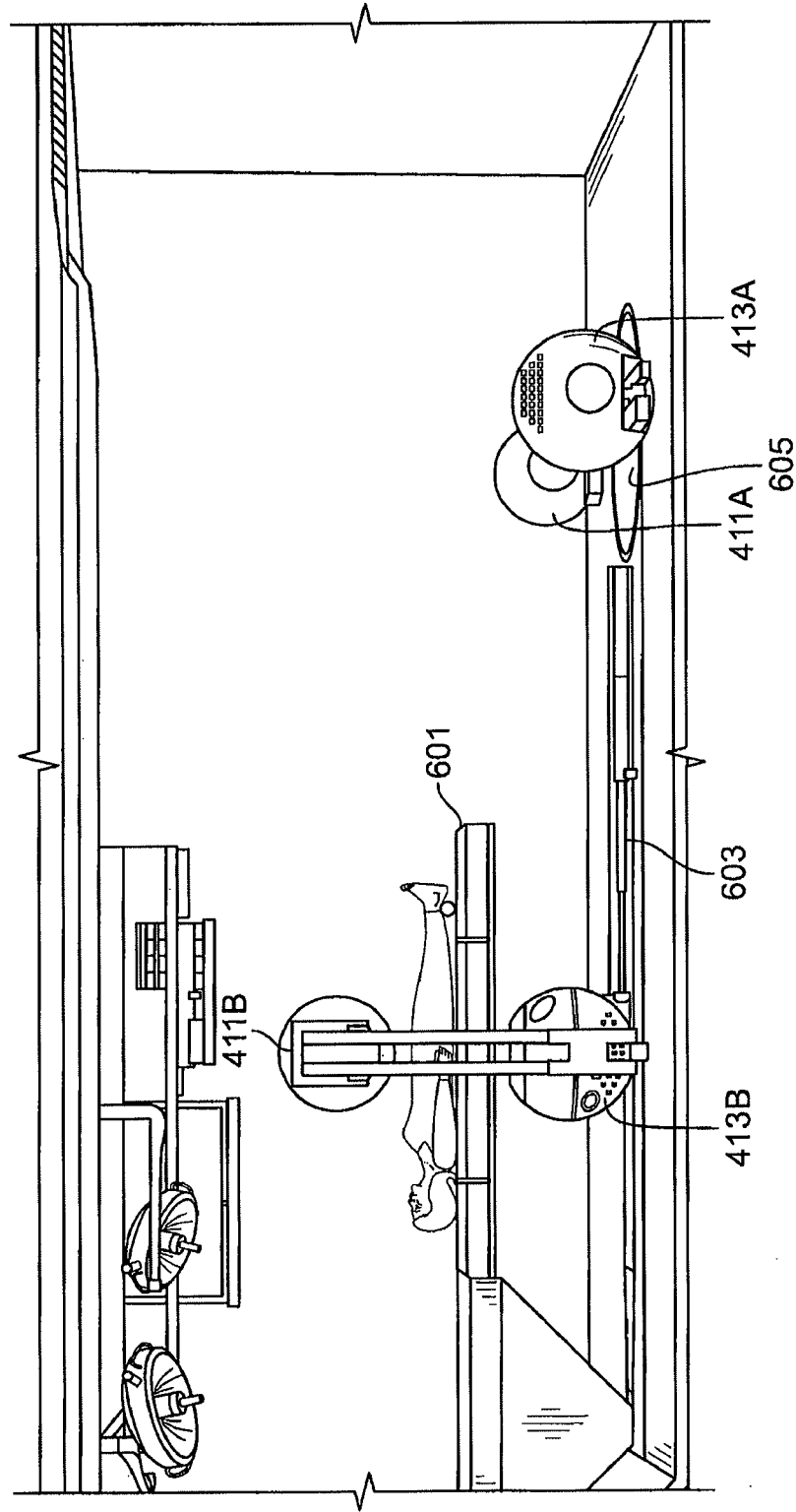
FIG. 6 is a perspective view of an examination room equipped with an imaging system that includes a rotating turntable within a first imaging volume and tracks for moving the x-ray generator and image detector into position around a second imaging volume.

FIG. 6 shows an exemplary radiography examination room equipped with an embodiment of the system 101. The embodiment shown in FIG. 6, includes the x-ray generator 411, x-ray detector 413, and robotic arms 401, 403. The examination room includes an examination table 601, a pair of tracks 603 along opposite sides of the examination table 601 and a turntable 605 at the foot of the table 601. The examination room according to this example allows the x-ray generator 411 and the x-ray detector 413 to be moved between two different imaging volumes 602, 604 (shown in FIGS. 6A & 6B). The x-ray generator 411 and the x-ray detector 413 are referred to below as 411A and 413A, respectively, when in the first position and as 411B and 413B, respectively when in the second position.

Figure 6A:
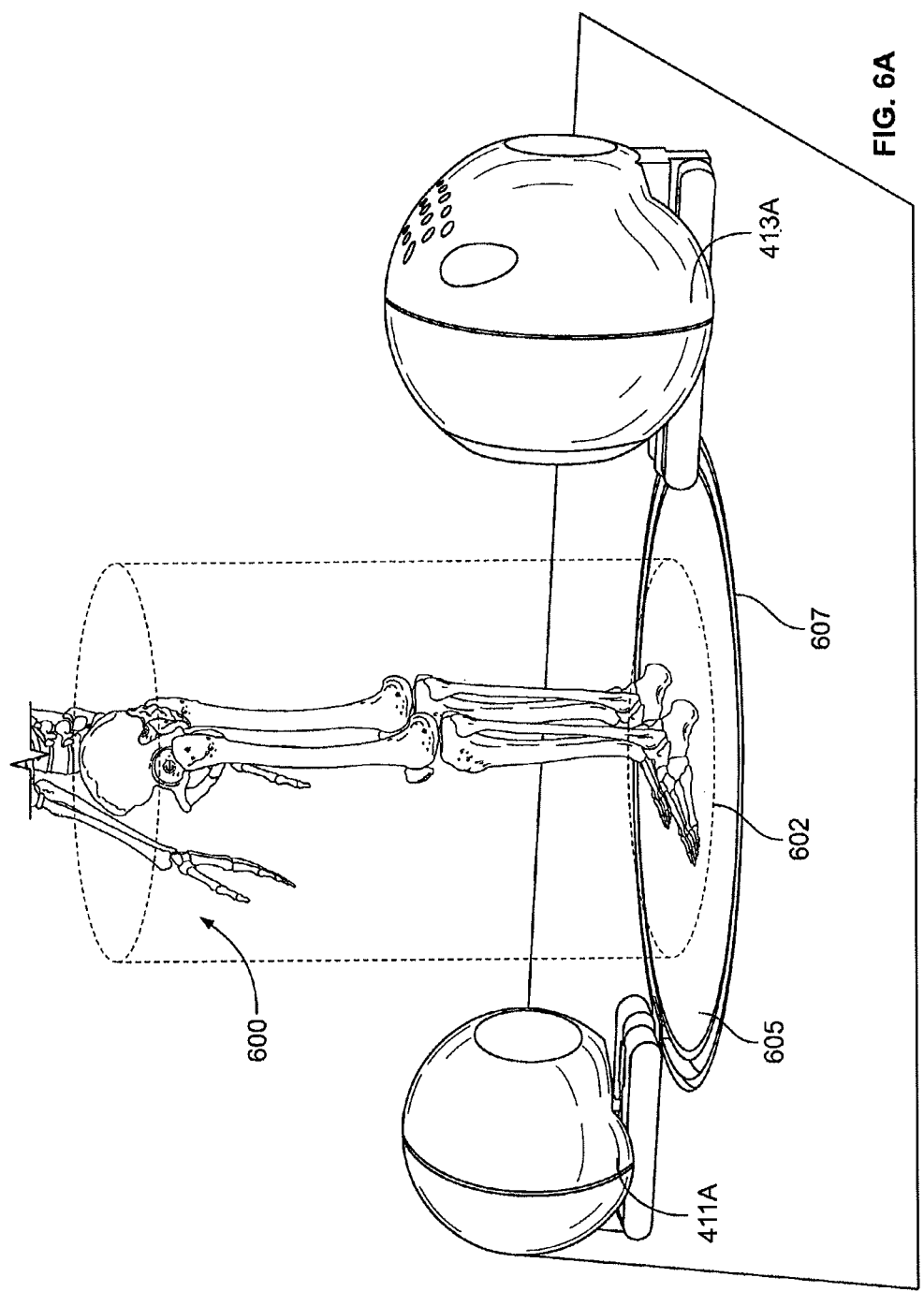
FIG. 6A is a perspective view showing the imaging system according to FIG. 5 positioned around the first imaging volume (i.e., a turntable).

In the first position, the x-ray generator 411A and the x-ray detector 413A are positioned on opposite sides of the turntable 605. In this position, the system can be used to capture images of a subject that is standing, seated, or performing a movement within a first imaging volume 602. FIG. 6A provides a more detailed view of the x-ray generator 411A and the x-ray detector 413A when in the first position. FIG. 6A shows an imaging subject 600 standing on turntable 605 within imaging volume 602. In this position, the turntable 605 can be rotated to capture images of the standing subject 600 from different perspectives. This rotational movement can be used to capture the images required to generate a three-dimensional, static CT model of the subject 600. The illustrated embodiment also includes circular track 607 to allow the x-ray generator 411A and the x-ray detector 413A to be rotated around a stationary imaging subject 600A. Furthermore, as described above, the height and angle of the x-ray devices can be changed to capture an image from another perspective. Because the system is capable of capturing images at a high frequency and reconstructing three-dimensional models of the imaging subject 600 in motion, in some embodiments, a device such as a treadmill can be placed in the first imaging volume 602 in addition to or instead of the turntable.

In the first position, the x-ray generator 411A and the x-ray detector 413A are positioned on opposite sides of the turntable 605. In this position, the system can be used to capture images of a subject that is standing, seated, or performing a movement within a first imaging volume 602. FIG. 6A provides a more detailed view of the x-ray generator 411A and the x-ray detector 413A when in the first position. FIG. 6A shows an imaging subject 600 standing on turntable 605 within imaging volume 602. In this position, the turntable 605 can be rotated to capture images of the standing subject 600 from different perspectives. This rotational movement can be used to capture the images required to generate a three-dimensional, static CT model of the subject 600. The illustrated embodiment also includes circular track 607 to allow the x-ray generator 411A and the x-ray detector 413A to be rotated around a stationary imaging subject 600A. Furthermore, as described above, the height and angle of the x-ray devices can be changed to capture an image from another perspective. Because the system is capable of capturing images at a high frequency and reconstructing three-dimensional models of the imaging subject 600 in motion, in some embodiments, a device such as a treadmill 606 can be placed in the first imaging volume 602 in addition to or instead of the turntable, as shown in FIG. 6C.

Figure 6B:
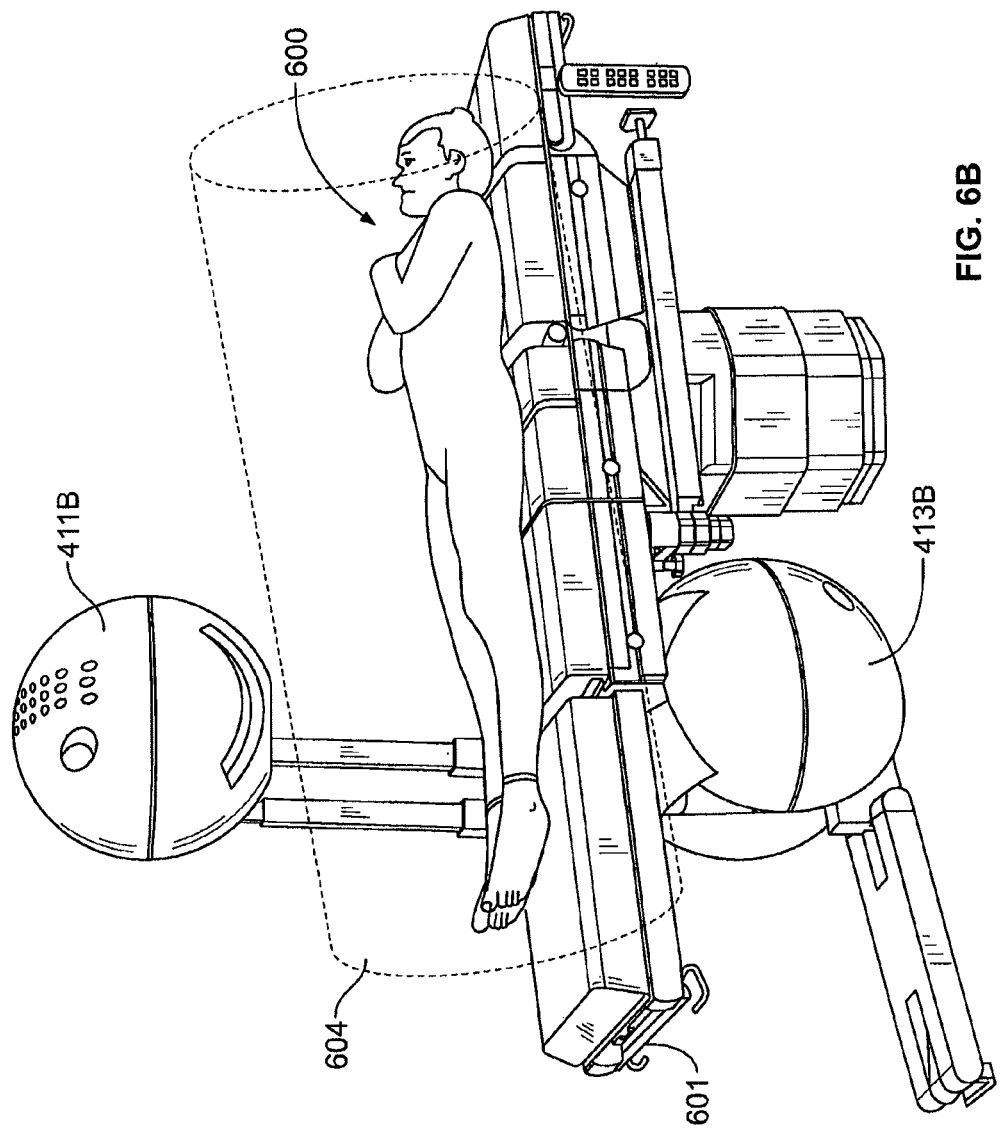
FIG. 6B is a perspective view showing the imaging system according to FIG. 5 positioned around a second imaging volume (i.e., an examination table).
Figure 6C:
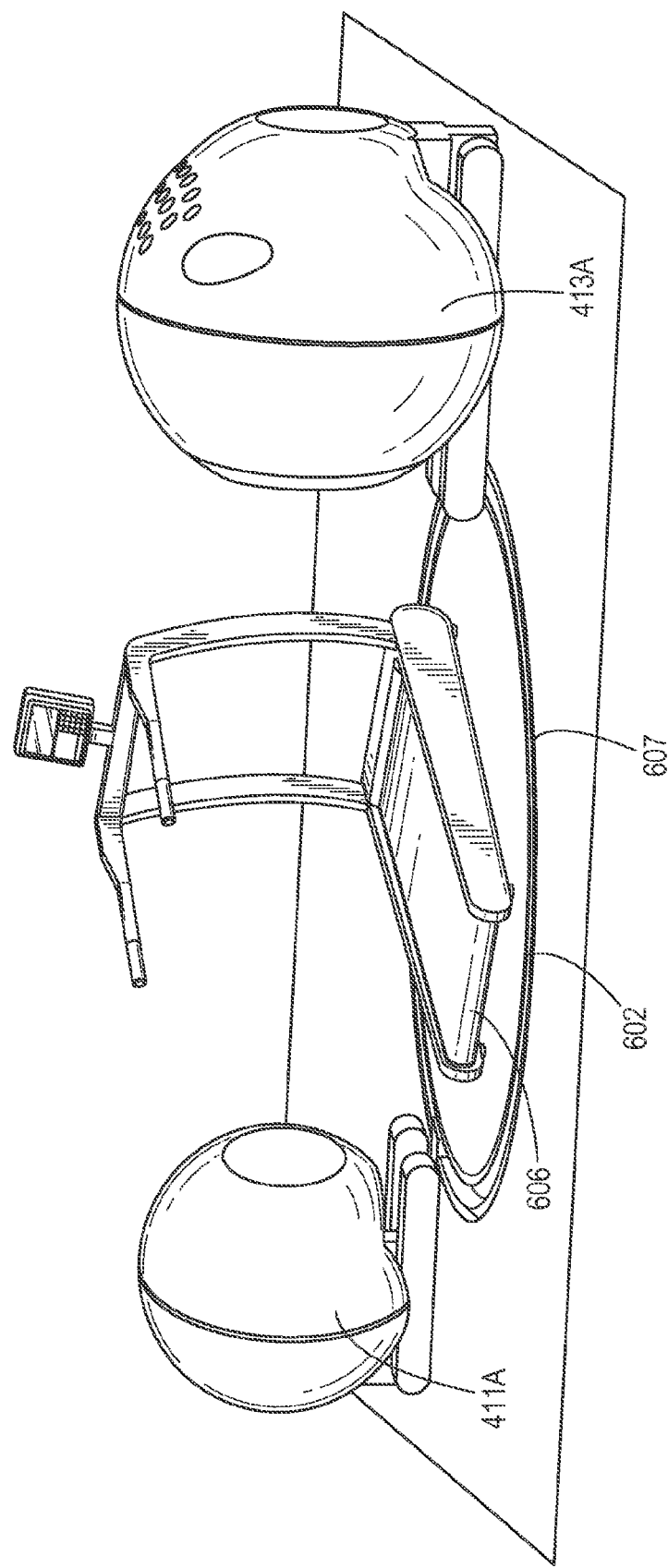
FIG. 6C is a perspective view showing the imaging system according to FIG. 5 positioned around another imaging volume (i.e., a treadmill).

Although, in the embodiment shown in FIGS. 6, 6A, and 6B, the robotic arms are connected to a series of tracks on the floor, the system is capable of other arrangements. For example, the circular track 607 and the parallel tracks 603 can be installed on the ceiling of a room such that the robotic arms, the x-ray generators, and the x-ray detectors are suspended from the ceiling and do not interfere with equipment or people located on the ground of the room. Furthermore, some embodiments to not include any tracks. In such embodiments, the base of each robotic arm is attached to wheels that allow the device to be moved freely and independently. The base in the wheeled-base systems may be weighted to lower the center of gravity of the system and to prevent the robotic arm from tipping.

Figure 7:
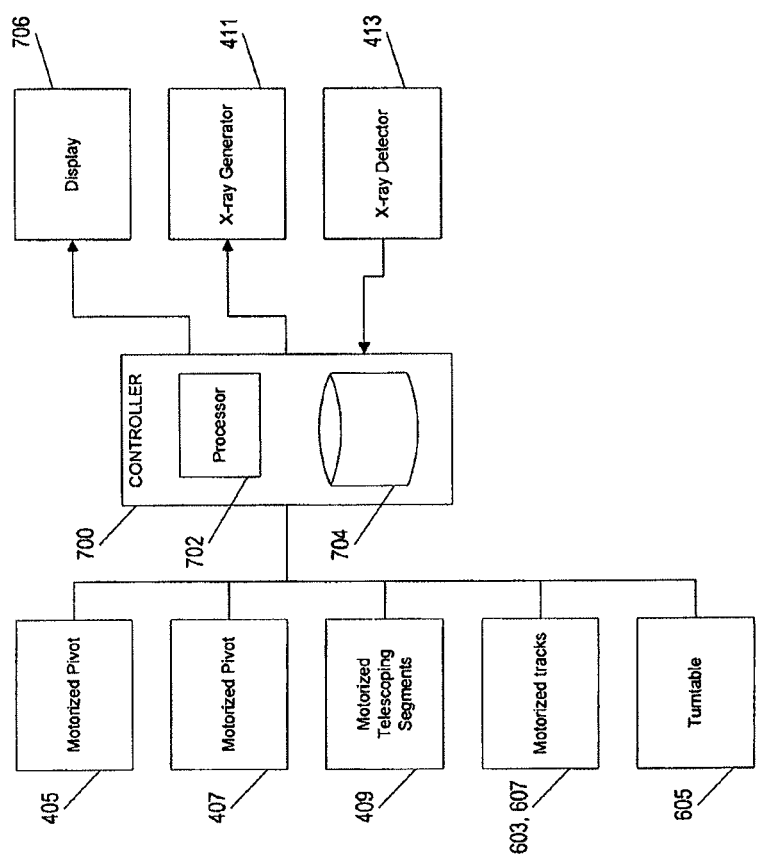
FIG. 7 is a block diagram of a controller according to one embodiment.

As shown in FIG. 7, a controller 700 is connected to the motors for each of the pivots 405, 407 and the telescoping segments 409 for the first robotic arm 401. The controller 700 also is connected to the motors that move the robotic arms along the circular track 111 shown in FIG. 1 or the parallel tracks 603 and the circular track 607 in FIGS. 6, 6A, and 6B. The controller 700 can be used to operate the turntable 605.

The controller 700 includes a processor 702 and a memory 704. In some embodiment, such as shown in FIG. 7, the same controller that operates that robotic arm also captures and processes images. The controller 700 sends a signal to x-ray generator 411 to initiate the transmission of x-rays. The controller 700 then receives x-ray image data from the x-ray detector 413. The controller 700 processes the image data (as described in detail below) and displays image information to the user on a display 706.

In some embodiments, the controller 700 is a desktop computer running appropriate software. In other embodiments, the controller 700 is integrated into the housing of either the x-ray generator 411 or the x-ray detector 413. In still other embodiments, the controller 700 is separated into two separate units—one that controls the movement of the robotic arms and a second that performs the image processing.

Each x-ray generator/detector pair described above can be used to capture two-dimensional radiographic images. Because the system can be configured to capture multiple two-dimensional images in rapid succession, the system is also capable of two-dimensional videoradiography. However, the system is also capable of more advanced three-dimensional modeling including rotational static CT volumetric rendering, tomosynthesis, marker-based biplane stereophotogrammetry, and markerless dynamic estimation of volumetric position. These three modalities are described in further detail below.

As described above, the system is capable of rotating the imaging subject relative to the x-ray generator 411 and the x-ray detector 413. This can be performed by moving the robotic arms around the circular track while keeping the subject stationary, rotating the subject on the turntable while the robotic arms remain stationary, or by rotating both the turntable and the robotic arms in opposite directions. By rotating the x-ray generator 411 and the x-ray detector 413 relative to the imaging subject, the system is able to capture a series of two-dimensional radiographic images of the stationary subject from many different perspectives. The series of images can then be used to construct a three-dimensional volumetric model of the imaging subject. Software applications, such as COBRA, are currently available that construct such volumetric models from a series of two-dimensional radiographic images.

Systems that include two-pairs of x-ray generators 411 and x-ray detectors 413 are capable of generating static or dynamic three-dimensional images using bi-plane stereophotogrammetry. Stereophotogrammetry generally uses triangulation to reconstruct a three-dimensional model from two or more two-dimensional images. In some embodiments, one or more tantalum (or other) markers are implanted within the subject patient. The markers provide reference points that are then identified by the data processor in each of the plurality of captured images. Such common reference points are used to reconstruct the three-dimensional digital model using stereophotogrammetry.

Figure 8:
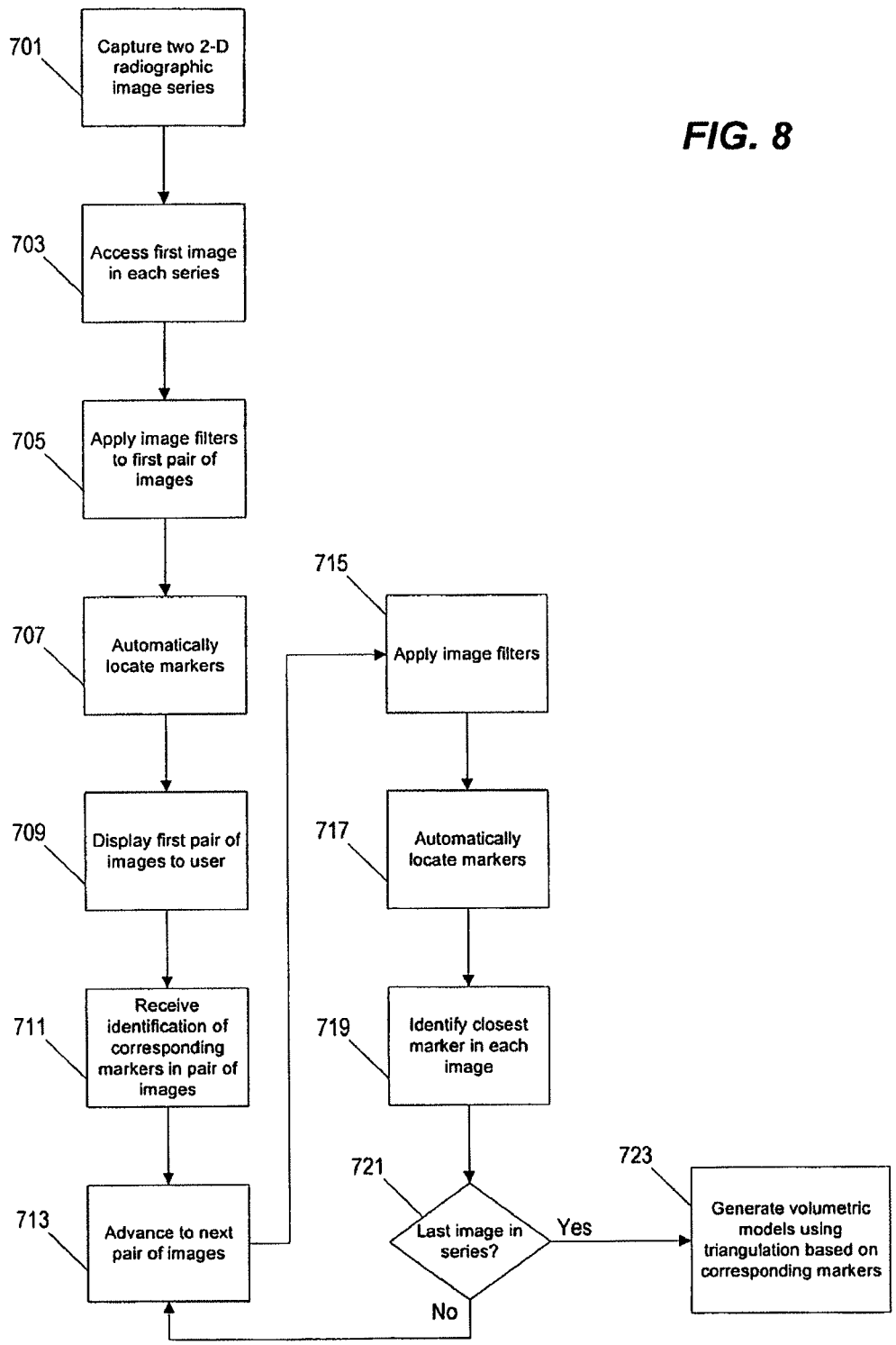
FIG. 8 is a flowchart of a method of generating a three-dimensional model using marker-based biplane stereophotogrammetric analysis.

FIG. 8 illustrates one method of performing biplane stereophotogrammetry using the system described above. This method can be performed, for example, on an interface system designed specifically for use with the image capturing system or by a personal computer running a software application. The system captures a first series of radiographic images from a first perspective and, at the same time, a second series of radiographic images from a second perspective (step 701). The data processing unit accesses the first image in each series (step 703) applies image processing routines such as Laplacian filter and Canny edge detection to the marker's geometric properties (step 705). The system then identifies the markers in each of the two images (step 707). A 5×5 Laplacian filter is applied on a small area around the region of the marker in order to enhance contrast and to remove background information. The output image is a result of summarized multiplications among the 5×5 mask values and the input image.

The first pair of images are then presented to the operator through a graphical user interface (step 709). The operator selects corresponding markers in the first pair of image and labels them (step 711). The data processing system then advances to the next pair of images in the series (step 713), performs image filtering (step 715), and locates the markers in each image (step 717). The data processing system automatically labels the markers in the second pair of images by identifying the marker that is closest to a labeled marker in the previous image (step 719). The data processor repeats this process until all of the two-dimensional images in each of the series has been processed (step 721). Once the markers have been identified in both of two corresponding images, the data processing system is able to generate a three-dimensional model of the imaging subject using triangulation (step 723). This triangulation process can be performed after each pair of images is processed or after all of the images in each series has been processed.

The system described above is also capable of estimating the position of an imaging subject and generating a dynamic three-dimensional model of a moving imaging subject without requiring the use of markers. This method of volumetric modeling begins with a CT scan or other volumetric model of an imaging subject and estimates the orientation of the imaging subject based on additional two-dimensional images captured by two x-ray detectors. Based on the assumption that a properly oriented projection through a 3D volumetric model (as captured by a CT scan) will produce an image similar to the radiographic images, embodiments identify common locations on the imaging subject (e.g., bone or prosthesis) using similarity matching based on the texture and rough edges of the imaging subject. Because this method estimates the orientation of a previously captured three-dimensional volumetric model, the image processing system does not need to perform the complex triangulation computations required to generate a dynamic three-dimensional representation based on two-dimensional radiographic images alone.

Figure 9:
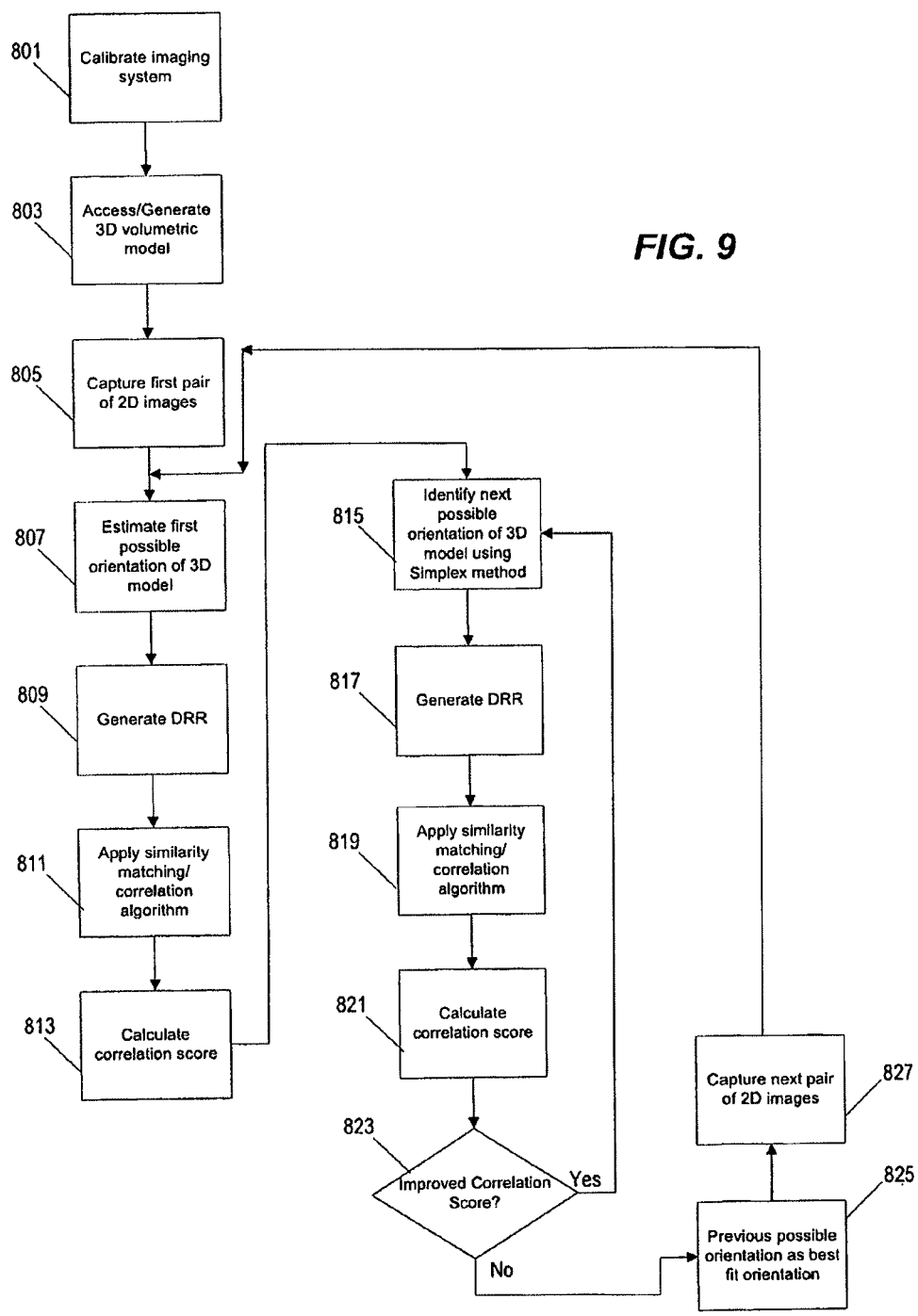
FIG. 9 is a flowchart of a markerless method of representing the movement of an imaging subject by estimating the appropriate orientation of a volumetric model.

FIG. 9 illustrates one example of this markerless process. The process begins by calibrating the imaging system to determine the imaging geometry using a 12-marker 3D calibration cube (step 801). The calibration cube is positioned in the view area of the biplane system, and biplane radiographs are captured. Positions of each marker are then calculated to determine the configuration of the biplane system relative to the global reference coordinate system using the Direct Linear Transformation (DLT) method.

Each single-plane system, green and red (denoted by "g" and "r" respectively), of the biplane system is described with extrinsic and intrinsic parameters. Extrinsic parameters consist of the position and rotation of the X-ray source of the single-plane system in the global reference coordinate system. For the green (red) system, a position vector, $^{ref}P_{gs}$ ($^{ref}P_{rs}$), a rotation matrix, $^{ref}R^g$($^{ref}R^r$) are determined from the DLT method. Intrinsic parameters include the principal point and the principal distance of the single-plane system. The principal point, $^gPP$ ($^rPP$), is the location in the image plane of the green (red) system, perpendicular to the center of the X-ray beam. The principal distance, $^gPD$ ($^rPD$), is the distance from the X-ray source to the principal point of the green (red) system. The intrinsic parameters, along with the size and resolution of the radiographic image, are sufficient to accurately simulate two single-plane radiograph systems. The extrinsic parameters are used to reconstruct the biplane system for determining the absolute 3D pose of the imaging subject in the global reference coordinate system.

The image processing system then accesses a three-dimensional volumetric model of the imaging subject (step 803). This volumetric model can be previously stored to memory or captured by the system by rotating the x-ray detector 413 and x-ray generator 411 relative to the imaging subject as described above. After the three-dimensional volumetric model is accessed, the system captures a first pair of two-dimensional radiographic images (step 805). As described above, the pair of images is captured by positioning two x-ray detectors 413 at different angles relative to the imaging subject. In some embodiments, a time-stamp incorporated into each two-dimensional radiographic image as metadata to indicate the time at which the image was captured. The timestamps are used to identify two corresponding images captured by each of the two x-ray detectors.

In some situations, the simultaneous use of two x-ray sources and two x-ray detectors in the same imaging volume can interfere with the quality of the captured images. X-rays from the first x-ray source can cause a scatter effect that appears in the image captured by the second x-ray detector. As such, some embodiments use a pulse sequencing method to offset the images captured by the first and second x-ray detectors by half of a frame. The first x-ray source emits x-rays that are detected by the first x-ray detector. The second x-ray source then emits x-rays that are detected by the second x-ray detector. The two x-ray detectors continue to alternate until sufficient data is captured. In these embodiments, an image captured by the first x-ray detector is matched with the image from the second x-ray detector that includes the next subsequent time stamp to provide the pair of images required for the stereophotogrammetric modeling.

Figure 10:
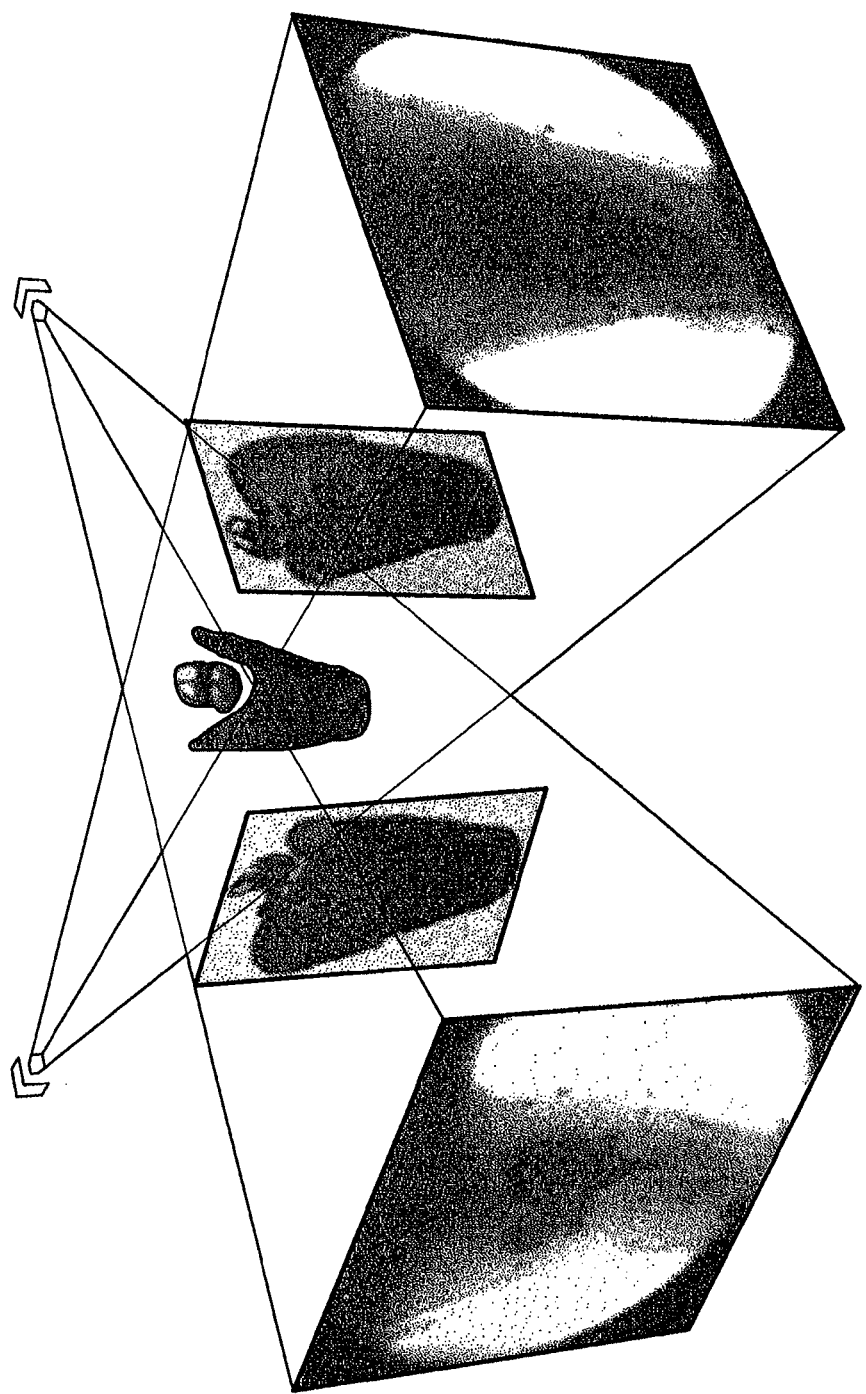
FIG. 10 is a perspective view illustrating the use of ray casting to generate a digitally simulated radiograph.

After a pair of two-dimensional radiographic images is captured, the system then selects a first possible orientation of the volumetric model based on the captured images (step 807). This selection can be based on a general similarity matching algorithm or selected arbitrarily. A digitally simulated radiograph (DSR) is then generated from the CT volumetric model based on the first possible orientation (step 809). A DSR may also be referred to as a digitally reconstructed radiograph (DRR). A DSR is a simulation of a conventional two-dimensional radiograph image based on data in a CT volumetric model. To simulate a desired orientation, the digital volume is rotated to orient the model properly and then re-sampled in memory to create equally spaced planes perpendicular to the principal axis (e.g., the direction of the x-ray beam if the image were being captured by a conventional x-ray detector. Each pixel of the DSR is calculated by summing re-sliced pixels along a ray from the source perspective to the image plane. This process is referred to as "ray casting." The principle of ray casting is illustrated in the image of FIG. 10. Vectors are traced from a hypothetical x-ray source, through the volumetric model, and to an imaging plane. The DSR is created by summing the value of all pixels along each vector.

Both the DSR and the radiographic images are preprocessed using the same processing algorithms to maximize similarity. First, each image is inverted and contrast-enhanced using a histogram-equalization algorithm. Then an edge-finding algorithm (such as, for example, the Sobel edge detector), is applied to extract edges from both the DSR and the radiographic images. The edge information is then added back to the original image.

To determine optimal position matching, a metric for similarity between two images is applied (step 811). A general normalized correlation is applied to the summed edge/intensity images. One such correlation equation is:

$$V(x, y) = \frac{\sum_{x,y} [r(x, y) - \overline{r_{u,v}}][m(x - u, y - v) - \overline{m}]}{\left\{\sum_{x,y} [r(x, y) - \overline{r_{u,v}}]^2 \sum_{x,y} [m(x - u, y - v) - \overline{m}]^2\right\}^{1/2}}$$

where:
r(x,y) is a pixel in the radiographic image
m(x,y) is a pixel in the DSR generated from the 3D CT model
$r_{u,v}$ is the mean pixel value of the DSR
m is the mean pixel value of radiographic image in the region under the DSR.

Figure 11:
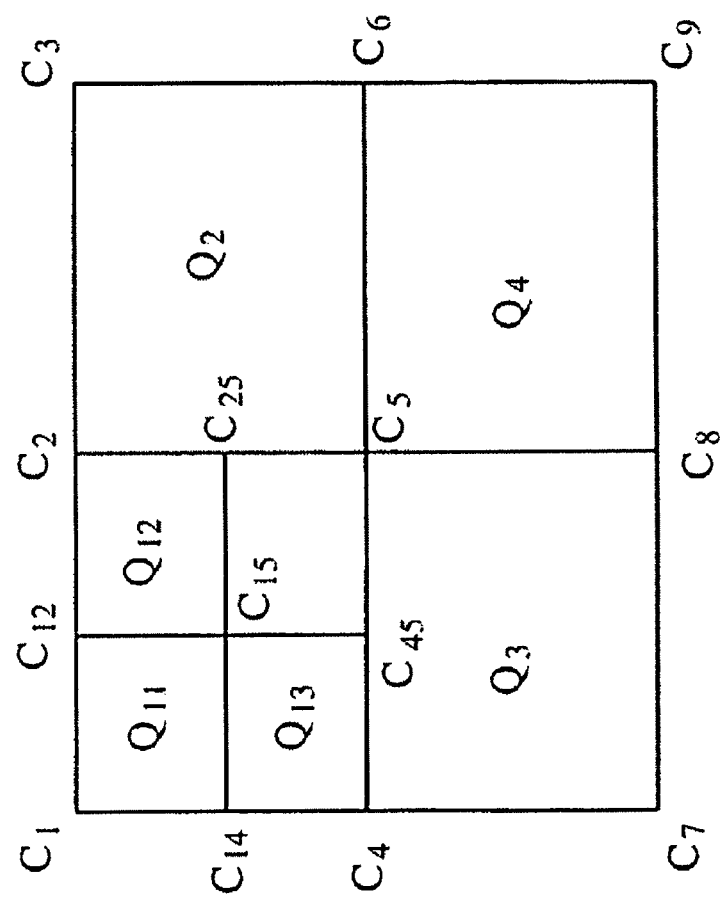
FIG. 11 is a quadtree-based correlation graph divided into four regions.

A Quadtree-based normalized correlation method may be employed to reduce search iterations and improve optimization efficiency. A predefined search space of the radiographic image is divided into four quadrants (as shown in FIG. 11). The average correlation value (ACq1, ACq2, ACq3, ACq4) of each quadrant (Q1, Q2, Q3, Q4) is calculated from correlation values of four corner points of the corresponding quadrant. The quadrant with the best correlation is further divided into four quadrants for the next step. For example, if ACq1 is the optimal average correlation value, ACq11, ACq12, ACq13, and ACq14 are calculated. This procedure continues until the size of a quadrant reduces to 4×4 pixels. In the final step, all pixels of the optimal quadrant of the radiographic image are correlated with the DSR (step 813).

The coordinate of the pixel with the best match is chosen as the location of the center in the image plane ($^{ref}p^{gm}$ and $^{ref}p^{rm}$). The value of the correlation function at this point is used as an indicator of the quality of match for the optimization process described below (see, step 823). The Quadtree algorithm is very efficient compared to other processes, particularly, for example, when used in circumstances where there is a maximum expected frame-to-frame translation of 20 pixels (40×40 pixel search region). Conventional sequential correlation would require 1600 image multiplications to find the best matching position, whereas the Quadtree-based correlation method requires only 40 multiplications.

Once pixels of the optimal quadrant are correlated, the image processing system then identifies a next possible orientation of the volumetric model based on the two-dimensional radiographic images (step 815). The image processing system then generates a DDR based on the new orientation (step 817), applies the similarity matching or correlation algorithm (step 819), and calculates a correlation score (step 821). If the correlation score improves in the second orientation (step 823), then the image processing system determines that the first possible orientation was incorrect. The system then identifies another possible orientation and repeats steps 817, 819, and 821. When the image processing system determines that the correlation score does not improve when a new orientation is selected (step 823), then the system determines that the previous orientation was the best match (step 825). After the best match orientation is identified, the system proceeds to capture the next pair of two-dimensional images (step 827).

Some embodiments use the downhill Simplex method to adjust the estimated position and orientation of the volumetric model until optimal similarity is obtained. The Simplex method requires N+1 points as starting points, where N is the number of degrees of freedom of the function being optimized. Then the Simplex method travels through the parameter space by reflection and contraction. Estimating 3D kinematics would typically require simultaneous optimization of all six motion parameters (three positions and three rotations). But in this method, movements parallel to the image plane (typically less than 20 cm) are considered small relative to the distance from the X-ray source to the bone (approximately 150 cm). Thus the effects of translations parallel to the image plane on the appearance of the projected bone are considered negligible. The center of the model is constrained to move along the principal axis and only three rotation parameters and the distance perpendicular to the image plane (out-of-plane position) are controlled by the optimization process to generate DSR's. The remaining two DOF parameters (in-plane position) are directly determined from correlation by finding the best-matching location in the image plane.

The optimization routine begins with five predefined perspectives (or vertices) (four DOF plus one, as required for Simplex method) as the starting points. DSR's for each vertex are generated from the 3D model using the known imaging geometry of a single-plane system and four DOF parameters (three orientation parameters and out-of-plane position parameter) controlled by the optimization process. Then two in-plane position parameters are determined from correlation between the DSR's and the radiographic images. Each reflection or contraction continues to update the three rotation parameters and the distance perpendicular to the image plane, based on the previous similarity calculations. The optimization routine is terminated when the distance of points moved in that step was fractionally smaller in magnitude than a predefined tolerance.

To check for local minima, the Simplex routine then restarts from the optimized point, and is allowed to converge again. If the new solution differed from the previous solution by more than a predefined tolerance (typically, 1° for rotation), the original solution was rejected as a local (non-global) minimum, and the routine is restarted from the new optimum point.

If sufficient computing resources are available, the calculations in the method illustrated in FIG. 9 can be performed in real-time. As illustrated in FIG. 8, the system captures a first pair of images (step 805), estimates the correct orientation of the volumetric model based on the images (steps 807-825), and then proceeds to capture the next image of the moving imaging subject (step 827). The estimated orientation of the volumetric model can then be displayed on a screen in real time as the imaging subject is moving. However, if computing resources are more limited, the series of two-dimensional radiographic images can be stored to memory and the system can then estimate the movement of the imaging subject based on the changing orientation of the volumetric model.

Additionally, a properly calibrated system is able to generate an estimated three-dimensional representation of the movement of an imaging subject using only a single x-ray generator 411 and a single x-ray detector 413 (i.e., a single-plane system). Six motion parameters can be estimated from a single-plane system for each frame (as opposed to the biplane system captured using two cameras). Because only a single x-ray generator 411 and x-ray detector 413 are used, a single-plane system only acquired a two-dimensional image of the imaging subject in a plane that is perpendicular to the path traveled by the x-rays from the x-ray generator 411 to the x-ray detector 413. As such, movements in the plane are readily detected. However, the accuracy for measuring out-of-plane translations is less accurate. Thus, only a projection ray passing from the X-ray source, through the center of the model, to the best-matching location in the image plane is constructed from each single-plane system. This projection ray is represented as a line segment connecting the X-ray source (the origin of a single-plane system) and the best-matching location in the image plane ($^gP_{gm}$ for the green system and $^rP_{rm}$ for the red system as determined by the calibration method described above).

The biplane system can be simulated in a single-plane system by estimating the distance between two points in the two-dimensional image based on a global reference coordinate system determine through calibration of the system. The position of the X-ray source is the origin of the single-plane system. Its location relative to the global reference coordinate system, $^{ref}P_{gs}$ ($^{ref}P_{rs}$) for a green (red) system, was already determined from the DLT calibration method described above. $^gP_{gm}$ ($^rP_{rm}$) is the location of one of the points from the two-dimensional image in a three-dimensional model and is transformed to the reference coordinate system by a rotation and a translation of the previously stored volumetric model according to the following equations:

$$^{ref}P_{gm} = {^{ref}R^g} P_{gm} + {^{ref}P_{gs}} \text{(for a green system)}$$

$$^{ref}P_{rm} = {^{ref}R^r} P_{rm} + {^{ref}P_{rs}} \text{(for a red system)}$$

where $^{ref}R^g$ ($^{ref}R^r$) is a 3×3 direction cosine matrix representing the orientation of the green (red) system with respect to the reference coordinate system.

$^{ref}P_{gm}$ ($^{ref}P_{rm}$) is the best-matching location in the image plane of the green (red) system transformed to the reference coordinate system.

Orientation of the volumetric model ($\alpha, \beta, \gamma$) is then determined from the estimated orientation ($^{ct}R_b$) of the bone model estimated in each single-plane system assuming body-fixed Y-X-Z rotations.

$^{ref}R_{gb} = {^{ref}R^g} \, {^gR^{ct}} \, {^{ct}R_b}$ for a green system and $^{ref}R_{rb} = {^{ref}R^r} \, {^rR^{ct}} \, {^{ct}R_b}$ for a red system, where $^{ct}R_b$ is a constant 3×3 direction cosine matrix of the orientation of the anatomical bone relative to the CT model. $^gR^{ct}$ ($^rR^{ct}$) is a 3×3 direction cosine matrix representing the orientation of the CT model with respect to the green (red) system, determined from single-plane optimization. $^{ref}R_{gb}$ ($^{ref}R_{rb}$) is the 3×3 direction cosine matrix of the bone expressed in the reference coordinate system. The final 3D orientation of the subject is determined by averaging the rotation angles obtained from the single-plane views:

$$\alpha = \frac{\alpha_{gm} + \alpha_{rm}}{2}$$

$$\beta = \frac{\beta_{gm} + \beta_{rm}}{2}$$

$$\gamma = \frac{\gamma_{gm} + \gamma_{rm}}{2}$$

As such, the invention provides for systems of capturing and displaying dynamic radiographic images. The invention also provides systems and methods of capturing biplane images and reconstructing a dynamic three-dimensional volumetric model of the subject using stereophotogrammetry. The invention also provides systems and methods for representing the estimated movement of an imaging subject based on a previously stored volumetric model and dynamic two-dimensional radiographic images. Various features and advantages of the invention are set forth in the following drawings and claims.

What is claimed is:

1. A medical imaging system, comprising:
   a first x-ray image detector;
   a first x-ray generator mounted opposite the first x-ray image detector such that x-rays are projected from the first x-ray generator to the first x-ray image detector through a first imaging volume;
   a second x-ray image detector;
   a second x-ray generator, wherein the second x-ray generator is mounted opposite the second x-ray detector such that x-rays are projected from the second x-ray generator to the second x-ray image detector through the first imaging volume and wherein the second x-ray image detector and the second x-ray generator are positioned at an angle relative to the first x-ray generator and the first x-ray image detector;

a rotational mechanism configured to perform at least one act selected from a group consisting of rotating an imaging subject within the first imaging volume and rotating the first x-ray image detector around the first imaging volume; and a controller configured to
capture volumetric data using the first x-ray detector and the rotational mechanism when operating in a first mode, and
capture stereophotogrammetric data using the first x-ray detector and the second x-ray detector concurrently when operating in a second mode.

2. The medical imaging system according to claim 1, wherein the controller is operable to control the rotational mechanism.

3. The medical imaging system according to claim 2, wherein the controller is further configured to operate the first x-ray image detector and the first x-ray generator.

4. The medical imaging system according to claim 1, wherein the first x-ray image detector is mounted on a first base, the first base including a first plurality of wheels and wherein the first x-ray generator is mounted on a second base, the second base including a second plurality of wheels.

5. The medical imaging system according to claim 1, wherein the rotational mechanism includes a circular track.

6. The medical imaging system according to claim 5, wherein the first x-ray image detector and the first x-ray generator are moveable along the circular track to position the first x-ray image detector and the first x-ray generator at an angle on the horizontal plane relative to the subject.

7. The medical imagining system according to claim 1, wherein the rotational mechanism includes a motorized turn-table that supports an imaging subject and rotates the imaging subject relative to the first x-ray image detector.

8. The medical imaging system according to claim 7, further comprising a treadmill that is interchangeable with the motorized turn-table to be mounted below the first imaging volume and between the first x-ray image detector and the first x-ray generator.

9. The medical imaging system according to claim 1, further comprising a pair of parallel tracks that move the first x-ray image detector and the first x-ray generator from a first imaging volume to a second imaging volume.

10. The medical imaging system according to claim 9, wherein the first x-ray image detector is movable along the first track and the first x-ray generator is movable along the second track.

11. The medical imaging system according to claim 10, further comprising a treadmill that guides the movement of an imaging subject in the second imaging volume.

12. The medical imaging system according to claim 11, wherein the first x-ray generator and the first x-ray image detector are rotatable around the treadmill in a horizontal plane.

13. The medical imaging system according to claim 1, wherein the first x-ray image detector includes an image intensifier and a high-speed digital camera.

14. The medical imaging system according to claim 13, wherein the high speed digital camera is attached to a housing by a clamping mechanism to allow for multiple cameras to be interchanged depending upon the specific application for which the system is being used.

15. The medical imaging system according to claim 1, wherein the first x-ray image detector includes a scintillator and a high-speed digital camera.

16. The medical imaging system according to claim 15, wherein the high-speed digital camera is attached to a housing by a clamping mechanism that allows for multiple cameras to be interchanged.

17. The medical imaging system according to claim 1, further comprising an image processing system coupled to the first x-ray detector, wherein the image processing system receives a series of images from the first x-ray detector and displays a videoradiographic image of an imaging subject.

18. The medical imaging system according to claim 1, further comprising an image processing system coupled to the first x-ray image detector and the second x-ray image detector, wherein the image processing system
receives an image from the first x-ray image detector and an image from the second x-ray image detector,
accesses a stored three-dimensional model of an imaging subject, and
positions the three-dimensional model on a display using stereophotogrammetry based on the image from the first x-ray image detector and the image from the second x-ray image detector.

19. The medical imaging system according to claim 1, further comprising an image processing system coupled to the first x-ray image detector and the second x-ray image detector, wherein the image processing system
receives a series of images from the first x-ray image detector and a series of images from the second x-ray image detector,
accesses a stored three-dimensional model of an imaging subject, and
generates a three-dimensional videoradiographic digital representation of an imaging subject in motion using stereophotogrammetry based on the series of images from the first x-ray image detector and the series of images from the second x-ray image detector.

* * * * *